(12) United States Patent
Desjarlais

(10) Patent No.: US 7,231,328 B2
(45) Date of Patent: Jun. 12, 2007

(54) APPARATUS AND METHOD FOR DESIGNING PROTEINS AND PROTEIN LIBRARIES

(75) Inventor: John R. Desjarlais, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 92 days.

(21) Appl. No.: 09/877,695

(22) Filed: Jun. 8, 2001

(65) Prior Publication Data

US 2002/0147547 A1    Oct. 10, 2002

Related U.S. Application Data

(60) Provisional application No. 60/266,711, filed on Feb. 6, 2001.

(51) Int. Cl.
G06G 7/58    (2006.01)
G06F 19/00    (2006.01)

(52) U.S. Cl. .............................. 703/2; 703/11; 702/27

(58) Field of Classification Search ................ 702/27; 530/333
See application file for complete search history.

(56) References Cited

U.S. PATENT DOCUMENTS

| 6,188,965 | B1 | 2/2001 | Mayo et al. | |
|---|---|---|---|---|
| 6,269,312 | B1 * | 7/2001 | Mayo et al. | ............... 702/19 |
| 6,403,312 | B1 | 6/2002 | Dahiyat et al. | |
| 2002/0123846 | A1 | 9/2002 | Miller et al. | |

OTHER PUBLICATIONS

Shaojian Sun. "Reduced representation model of protein structure prediction: Statistical potential and genetic algorithms." *Protein Science*. (1993), 2, 762-785.
Fujiyoshi-Yoneda. "Adaptability of restrained molecular dynamics for tertiary structure prediction: application to Crotalus atrox venom phospholipase A2." *Protein Engineering*. (1991), vol. 4, 443-450.
International Search Report. PCT/US02/03789, mailed Jan. 22, 2003.
Dahiyat et al. "Automated design of the surface positions of protein helices." *Protein Science*. (1997), 6: 1333-1337.
Dahiyat et al. "Protein design automation." *Protein Science*. (1996), 5: 895-903.
Dahiyat et al. "De novo protein design: Fully automated sequence selection." *Science*. vol. 278, Oct. 3, 1997, 82-87.
Dahiyat et al. "Probing the role of packing specificity in protein design." *Proc. Natl. Acad. Sci. USA*. vol. 94, 10172-10177, Sep. 1997.
Dahiyat et al. "De novo protein design: Towards fully automated sequence selection." *J. Mol. Biol.* (1997) 273, 789-796.
Delarue et al. "The inverse protein folding problem: Self consistent mean field optimisation of a structure specific mutation matrix." *Pac Symp Biocomput*. (1997), 109-121.
Desjarlais et al. "Computer Search Algorithms in protein modification and design." (1998) *Curr Opin Struct Biol*. 8(4). 471-5.
Desjarlais et al. "De novo design of the hydrophobic cores of proteins." *Protein Science* (1995), 4, 2006-18.
Desjarlais et al. Side-chain and backbone flexibility in protein core design. *J. Mol. Biol*. (1999), 290(1), 305-18.
Desmet et al., "The dead-end elimination theorem and its use in protein side-chain positioning." *Nature*. (1992), 356(9), 539-542.
Dunbrack et al. Bayesian statistical analysis of protein side-chain rotamer preferences. *Protein Sci*. (1997), 6(8), 1661-81.
Eisenberg et al., "Solvation energy in protein folding and binding," *Nature*. 319, 199-203, 1986.
Goldstein. Efficient rotamer elimination applied to protein side-chains and related spin glasses. *Biophys. J.* (1994), 66(5), 1335-40.
Gordon. Energy functions for protein design. *Curr Opin Struct Biol*. (1999), 9(4), 509-13.
Harbury et al. "Repacking protein cores with backbone freedom: structure prediction for coiled coils." *Proc Natl Acad Sci USA*. (1995), 92(18), 8408-12.
Hellinga. "Rational protein design: combining theory and experiment." *Proc Natl Acad Sci USA*. (1997), 94(19), 10015-17.
Hellinga et al. "Optimal sequence selection in proteins of known structure by simulated evolution." *Proc Natl Acad Sci USA*. (1994), 91(13), 5803-7.
Hendsch et al. Electrostatic interactions in the GCN4 leucine zipper: Substantial contributions arise from intramolecular interactions enhanced on binding. *Protein. Sci*. (1999), 8(7), 1381-92.
Henikoff et al. Position-based sequence weights. *J. Mol. Biol*. (1994), 243(4), 574-8.
Holland. *Adaptation in natural and artificial systems*. The MIT Press, Cambridge, MA (1992).
Johnson et al. Solution structure and dynamics of a designed hydrophobic core variant of ubiquitin. *Structure Fold Des*. (1999), 7(8), 967-76.
Jorgensen et al. "The OPLS potential functions for proteins. Energy minimizations for crystals of cyclic peptides and crambin." *J. Amer. Chem. Soc*. (1988), 110(6), 1657-1666.
Koehl et al. "Application of a self-consistent mean field theory to predict protein side-chains conformation and estimate their conformational entropy." *J. Mol. Biol*., 239(2), 249-75.
Koehl et al. "Mean-field minimization methods for biological macromolecules." *Curr Opin Struct Biol*., (1996), 6(2), 222-6.
Kono et al. "Energy minimization method using automata network for sequence and side-chain conformation prediction from given backbone geometry." *Proteins*. (1994), 19(3), 244-255.
Kono et al. "Designing the hydrophobic core of Thermus flavus malate dehydrogenase based on side-chain packing." *Protein Eng*. (1998), 11(1), 47-52.
Kuhlman et al. "Native protein sequences are close to optimal for their structures." *Proc. Natl. Acad. Sci. USA*. (2000), 97(19), 10383-8.
Lazar et al. "De novo design of the hydrophobic core of ubiquitin." *Protein Sci*. (1997), 6(6), 1167-78.

(Continued)

*Primary Examiner*—Marjorie A. Moran
(74) *Attorney, Agent, or Firm*—Fish & Richardson P.C.

(57) ABSTRACT

Methodology for the automated design of proteins is disclosed. Various methods executed by a computer for generating probability matrices, protein sequences, combinatorial libraries of proteins, and optimization of various parameters related to protein design are disclosed. Methodology is applicable to the design and analysis of protein structures and protein sequences.

25 Claims, 6 Drawing Sheets

OTHER PUBLICATIONS

Lazar et al. "Rotamer strain as a determinant of protein structural specificity." *Protein Sci.* (1999), 8(12), 2598-610.

Lee. "Predicting protein mutant energetics by self-consistent ensemble optimization." *J. Mol. Biol.* (1994), 236(3), 918-39.

Micheletti et al. "Design of proteins with hydrophobic and polar amino acids." *Proteins.* (1998), 32(1), 80-7.

Raha et al. "Prediction of amino acid sequence from structure." *Protein Sci.* (2000), 9(6), 1106-19.

Ranganathan et al. "Structural and functional analysis of the mitotic rotamase Pin 1 suggests substrate recognition is phosphorylation dependent." *Cell.* (1997), 89(6), 875-86.

Street et al. "Computational protein design." *Structure Fold Des.* (1999), 7(5), R105-9.

Su et al. "Coupling backbone flexibility and amino acid sequence selection in protein design." *Protein Sci.* (1997), 6(8), 1701-7.

Voigt et al. "Trading accuracy for speed: A quantitative comparison of search algorithms in protein sequence design." *J. Mol. Biol.* (2000), 299(3), 789-803.

Voight et al. "Computational method to reduce the search space for directed protein evolution." *Proc. Natl. Acad. Sci. USA.* (2001), 98(7), 3778-83.

Weiner et al. "A new force field for molecular mechanical simulation of nucleic acids and proteins." *Journal of the American Chemicical Society.* (1984), 106(3), 765-84.

\* cited by examiner

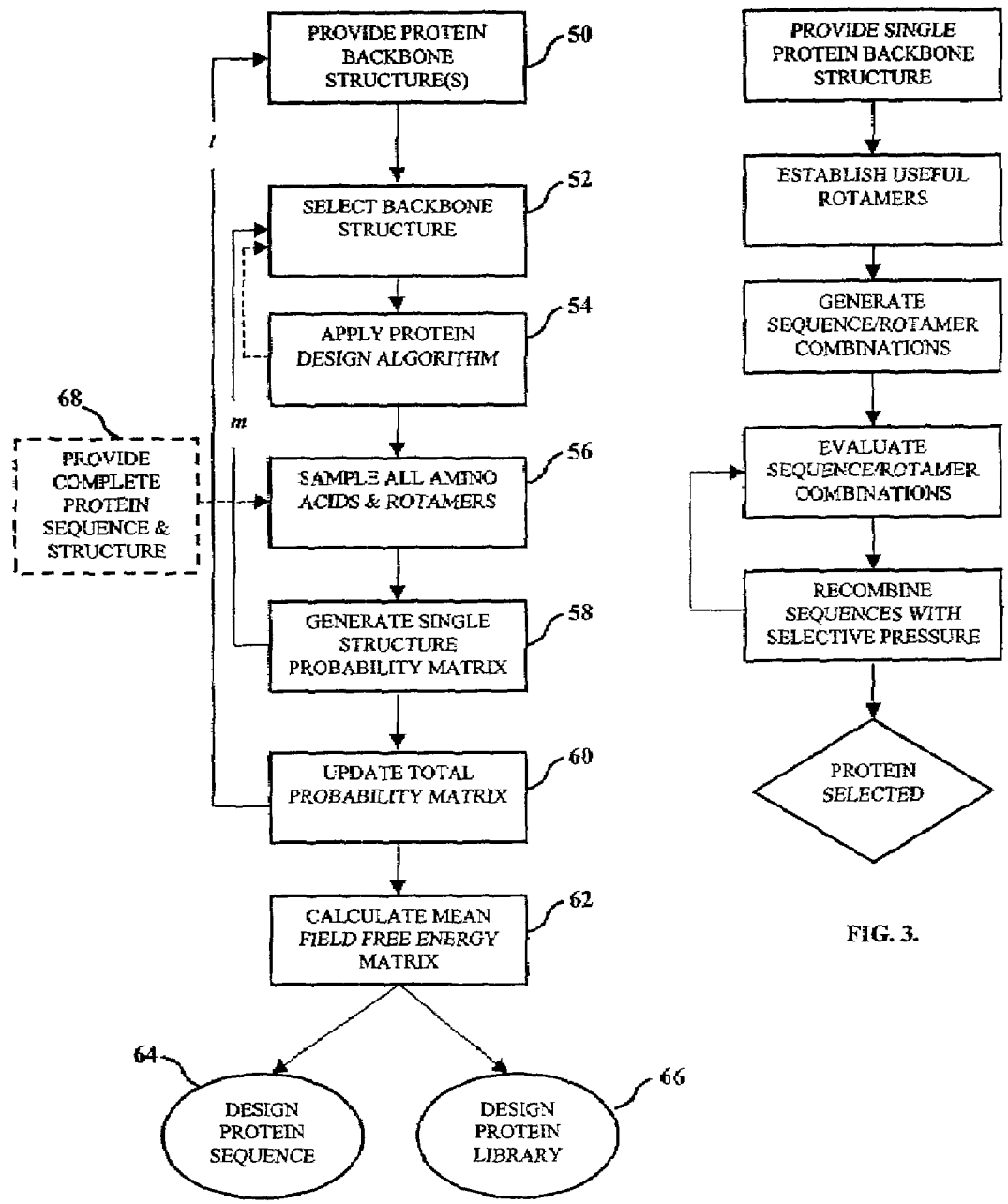

library design using free energy limits complexity ~ $10^5$

```
SLPSGWTQLTKASDDTTYYYNKTTDVVTNTRPTD
N         K K SG  N       Q SN  K    N    N
D         P    E                      Q
          V    S
          E
          R
```

FIG. 8B.

complexity ~ $10^8$

```
SLPSGWTQLTKASDDTTYYYNKTTDVVTNTRPTD
N         KQK SGNNSV  F   Q SNTKQD N    N
D         P     E         E QT     Q
E         V     S
          E
          R
          N
```

FIG. 8C.

library design using probability limit complexity ~ $10^5$

```
SLPSGWTQLTKASDDTTYYYNKTTDVVTNTRPTD
N         K K SGNN  V F   Q SN  KQ  N    N
D
```

FIG. 8.

APPARATUS AND METHOD FOR DESIGNING PROTEINS AND PROTEIN LIBRARIES

The present application is related to co-pending Provisional Application Ser. No. 60/266,711 of John R. Desjarlais filed Feb. 6, 2001, entitled "A method for ensemble-averaged calculations in computational protein design", based on which priority is herewith claimed under 35 U.S.C. 119(e) and the disclosure of which is incorporated herein by reference in its entirety.

This Provisional Patent Application was made with government support under grant number CHE-9876234 from the National Science Foundation. Accordingly, the U.S. government has certain rights in the invention.

FIELD OF THE INVENTION

The present invention relates to an apparatus and method for quantitative protein design and optimization.

BACKGROUND OF THE INVENTION

There has been considerable recent success in the development of computational methods for the design of protein sequences, at various degrees of sophistication. Several groups have presented results in which computer algorithms were used to design novel hydrophobic cores for proteins (Dahiyat & Mayo, 1996; Dahiyat & Mayo, 1997b; Desjarlais & Handel, 1995; Hellinga & Richards, 1994; Kono & Doi, 1994; Lazar et al., 1997), in many cases with experimental validation of the proteins by biophysical and/or structural methods (Dahiyat & Mayo, 1996; Dahiyat & Mayo, 1997b; Desjarlais & Handel, 1995; Johnson et al., 1999; Kono et al., 1998; Lazar et al., 1997; Lazar et al., 1999).

Mayo and colleagues have pioneered the development of algorithms for non-core (Dahiyat et al., 1997a) and full sequence design (Dahiyat & Mayo, 1997a; Dahiyat et al., 1997b), using parameterized force fields and sophisticated optimization methods such as the Dead-End Elimination (DEE) theory (Desmet et al., 1992; Goldstein, 1994). These methods were used successfully to design a sequence that adopts the zinc finger fold with no requirement for zinc binding (Dahiyat & Mayo, 1997a). The force fields used for these design processes have been parameterized over time by comparison between the calculated and experimentally determined folding stabilities of the designed proteins, a process referred to as the design cycle (Dahiyat & Mayo, 1996; Gordon et al., 1999; Hellinga, 1997; Street & Mayo, 1999). A patent related to these studies is U.S. Pat. No. 6,188,965, incorporation herein by way of reference.

A significant limitation (and criticism) of extant protein design methodologies is a lack of a generally applicable method for incorporating backbone flexibility into the design simulation. Although some efforts along these lines have been explored (Desjarlais & Handel, 1999; Harbury et al., 1995; Su & Mayo, 1997), they are limited in scope.

A second limitation in many design methods is that they do not provide a comprehensive measure of the sequence space that is consistent with a three-dimensional protein fold. In this context, sequence space means all sequential combinations of amino acids that can spontaneously fold into the target three-dimensional structure. Knowledge of the viable sequence space is a crucial feature of the ability to rationally design protein combinatorial libraries that can be used to search for proteins with improved properties.

Again, some efforts along these lines have been pursued, for instance by designing multiple sequences using heuristic (Monte Carlo or genetic algorithm) methods (Dahiyat et al., 1997b; Desjarlais & Handel, 1995; Kuhlman & Baker, 2000). Such methods serve to partially explore the sequence space of a fold, but do not necessarily yield quantitatively robust information. Application of the self-consistent mean field methods (Delarue & Koehl, 1997; Koehl & Delarue, 1994; Lee, 1994) has some promise for exploring sequence space (Voigt et al., 2001), but this class of methods have significant limitations that call into question their ability to fully explore the appropriate space (Voigt et al., 2000). Furthermore, this method has not yet been demonstrated to yield physically viable designed proteins.

In view of the previous discussion of demands and limitations in the field of protein design, it can be seen that there is a need to improve protein design and evaluation methodology. Accordingly, it is an object of the invention to provide a computational protein design procedure that is capable of incorporating backbone flexibility in a general way and is capable of providing a superior exploration of the amino acid sequence space consistent with a protein structural state. Another object of the invention is to provide a novel approach to the evaluation and parameterization of protein design algorithms that is more efficient than efforts that rely on feedback from experimental stability data alone. Yet another object of the invention is to provide a method of analysis of the ability of protein design algorithms to design amino acid sequences that are similar to those that exist naturally for a given protein class. These and other objects and advantages of the invention and equivalents thereof, are described and provided in the drawings and descriptions that follow and manifest in the appended claims.

SUMMARY OF THE INVENTION

In accordance with the objects outlined above, the present method provides methods executed by a computer under the control of a program, the computer including a memory for storing the program. The method comprising the steps of receiving a single or multiple protein backbone structures and analyzing the interaction of each of the rotamers with all or part of the remainder of the protein backbone structure or ensemble of backbone structures to generate a quantitative probabilistic representation of the amino acid sequence space consistent with the fold of the protein. The methods may further comprise the parameterization of the scoring functions and reference energies by comparison to natural protein sequence statistics and patterns.

In a further aspect of the invention, the probabilistic representation of the amino acid sequences consistent with the backbone structure can be used to derive a single high probability sequence for testing in the laboratory. The probabilities can also be used to guide the design and construction of combinatorial libraries of proteins for production, selection, or characterization in the laboratory.

In a further aspect, the invention provides a computer readable memory to direct a computer to function in a specified manner, comprising a side chain module to select useful rotamers, and an optimization module to generate designed protein sequences. The memory may further comprise a parameterization module to relate comparisons between the designed sequences and natural sequences that have desirable properties, such that the design algorithm is further optimized.

BRIEF DESCRIPTION OF THE DRAWINGS

FIG. 2 illustrates processing steps associated with an embodiment of the invention. Repeated application of a protein design algorithm together with processing steps unique to the invention leads ultimately to the creation of designed proteins or combinatorial libraries of proteins.

FIG. 3 illustrates the processing steps associated with a protein design algorithm in accordance with an embodiment of the invention. In particular, FIG. 3 illustrates the use of genetic algorithm optimization of side chains and rotamers, which is implemented at step 54 of FIG. 2 in a preferred embodiment of the invention. The central feature of the genetic algorithm is the cycling between evaluation of side chain and rotamer combinations, and the recombination of models containing different combinations of side chains and rotamers.

FIG. 5 illustrates a mean field free energy matrix for a WW domain (SEQ ID NO:1), generated in accordance with a preferred embodiment of the invention.

FIG. 8 illustrates the creation of combinatorial libraries using different strategies.

FIG. 8A shows a combinatorial library (SEQ ID NO:2) developed by slowly increasing an upper limit on free energy, according to the free energy matrix of FIG. 5, and a library complexity of $10^5$. FIG. 8B shows a combinatorial library (SEQ ID NO:3) developed by slowly increasing an upper limit on free energy, according to the free energy matrix of FIG. 5, and a library complexity of $10^8$. FIG. 8C shows a combinatorial library (SEQ ID NO:4) developed by slowly decreasing a lower limit on probability, according to a probability matrix derived from FIG. 5, and a library complexity of $10^5$.

DETAILED DESCRIPTION OF THE INVENTION

Figure 1:
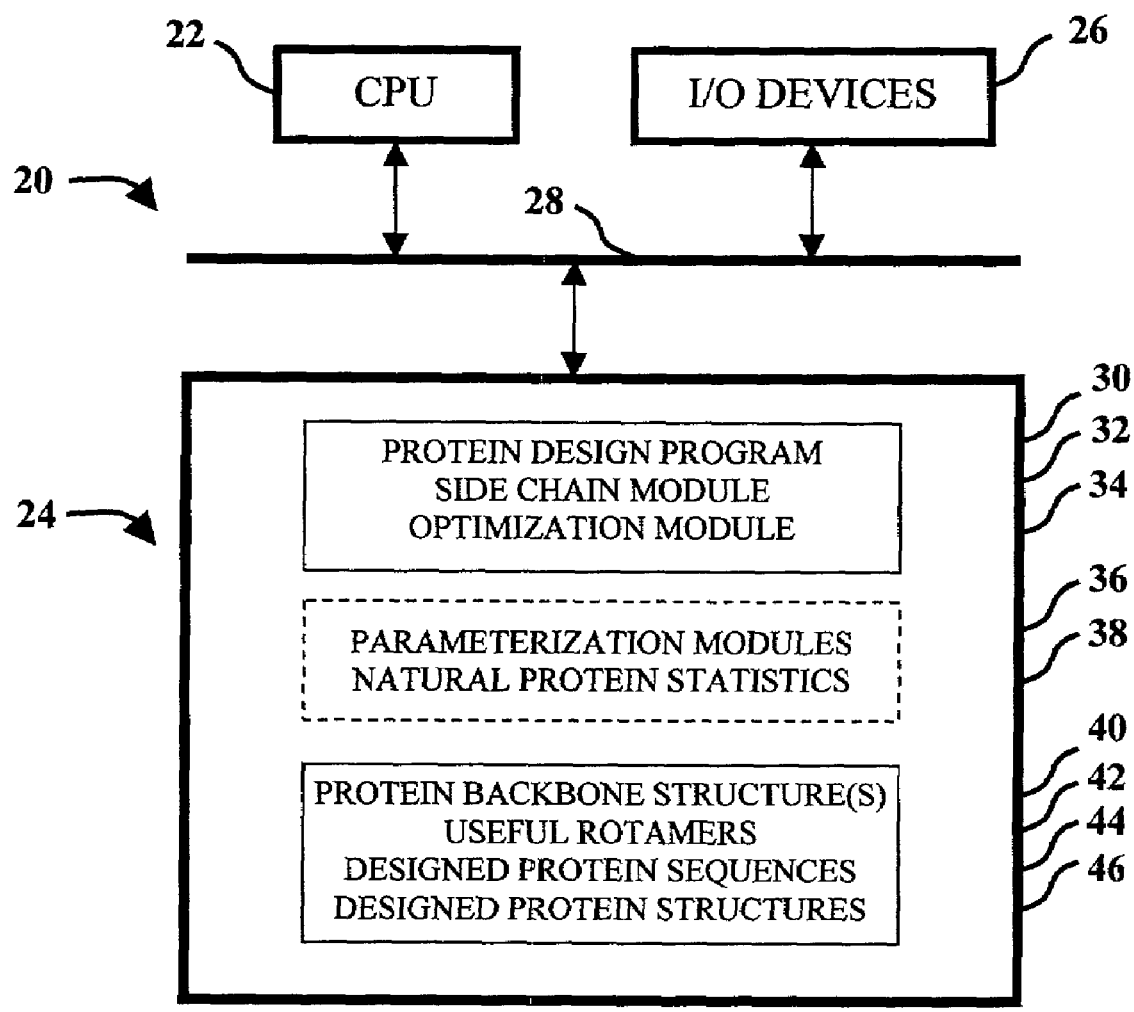
FIG. 1 illustrates a general purpose computer configured in accordance with an embodiment of the invention.

The present invention relates to the design of amino acid sequences that spontaneously adopt a predetermined three-dimensional structure. The target structure is defined by taking the backbone coordinates from the experimentally determined structure of an existing protein, usually derived from natural sources. Such structures are often readily available in the public domain. The present invention furthermore provides the capability of designing combinatorial libraries via a probabilistic representation of the space of amino acid sequences that are consistent with the target structure, within preset tolerance levels, such that a diverse set of sequences can be explored.

It will be appreciated by those skilled in the art that the designed proteins described herein can be encoded by nucleic acid sequences. Nucleic acid sequences encoding protein sequences generated by the methods of the invention may be placed in various eukaryotic or prokaryotic host cells and expressed by techniques known in the art. A variety of expression vectors and host cells may be used to obtain quantities of designed proteins. While small proteins may preferably be synthesized, larger designed proteins for which significant samples are desired may utilize an optimized protein sequence of the invention to create a nucleic acid such as DNA encoding said optimized sequence which can be conveniently cloned into a suitable host cell and expressed. Nucleic acids, particularly DNA, encoding optimized protein sequences may conveniently be made by use of materials and methods well known in the art. The choice of the various codons, expression vectors, methodology, and use of host cells, including both microbial and animal or plant systems, can conveniently be optimized as required. Also, as will be appreciated by those in the art, the designed proteins of the invention have a variety of applications ranging from large scale industrial uses, to various consumer products, to various pharmaceutical uses. In addition, those skilled in the art will appreciate and will be able to construct and maintain appropriate combinatorial libraries of designed proteins of the invention which may conveniently be selected and utilized for various applications.

In the general art of protein design, two components interact throughout a design simulation to produce candidate protein sequences. The first component is a scoring function that evaluates the quality of possible models of the protein. Such models consist of the input backbone structure, a linear sequence of amino acids, and a set of spatial orientations of the amino acids relative to the remainder of the structure. The side chain orientations are often grouped into classes of orientations or conformers called rotamers. The second major component of a design algorithm is an optimization protocol that is used to seek optimal combinations of amino acids and rotamer states as defined by the scoring function.

The present invention relates to unique developments in the protein design art, leading to improved abilities to incorporate backbone degrees of freedom, and an improved ability to provide a comprehensive view of the space of amino acid sequences consistent with the structure.

The present invention also provides methods for optimizing the relationship between the various terms in the scoring function, the relationship between the scoring function and the optimization procedure, and the relationship between these components and additional simulation parameters. This is achieved by comparing the features of designed proteins to natural proteins that have similar properties.

FIG. 1 illustrates an automated protein design apparatus 20 in accordance with an embodiment of the invention. The apparatus 20 includes a central processing unit 22 which communicates with a memory 24 and a set of input/output devices (e.g. keyboard, mouse, monitor, printer, etc.) 26 through a bus 28. The general interaction between a central processing unit 22, a memory 24, input/output devices 26, and a bus 28 is known in the art. The present invention is directed toward the automated protein design program 30 stored in the memory 24.

The automated protein design program 30 may be implemented with a side chain module 32. As discussed in detail below, the side chain module establishes a set of useful rotamers for a selected protein backbone structure. The protein design program 30 may also be implemented with an optimization module 34 that analyzes the interaction of rotamers with the protein backbone structure to generate optimal or near-optimal protein sequences. The protein design program 30 may also include a parameterization module 36 that is used to compare designed proteins to natural proteins such that the design program can be further optimized.

The memory 24 also stores one or a set of protein backbone structures 40, which is downloaded by a user through the input/output devices 26. The memory 24 also stores information on useful rotamers 42 derived by the side chain module 32. In addition, the memory 24 stores designed protein sequences 44, structures of designed proteins 46. Furthermore, the memory 24 stores natural protein statistics 38 for use by the parameterization module 36.

The operation of the automated protein design apparatus 20 is further detailed in FIG. 2, which illustrates the processing steps executed in accordance with the method of the invention. Most of the processing steps are executed by the protein design program 30.

The protein from which the input structure is derived may be any protein for which a three-dimensional structure is known or can be generated; that is, for which there are three-dimensional coordinates for each atom of the protein. Generally, said coordinates can be determined by X-ray crystallography, NMR spectroscopy, comparative modeling, or ab initio structure prediction. The protein may furthermore be from any organism, or may be an unnatural protein produced by protein design. In a preferred embodiment, only the protein backbone is required for application of the invention. By "protein backbone" is meant the three-dimensional coordinates of the nitrogen, alpha-carbon, carbonyl carbon, and the carbonyl oxygen of all or most of the amino acids of the protein.

A Typical Protein Design Algorithm: the Sequence Prediction Algorithm (SPA) (Raha et al., 2000)

A typical protein design algorithm produces a sequence or sequences that are consistent with a single input protein backbone structure. The present invention extends the capacity of protein design algorithms such that thermodynamic information from multiple backbone structures can be integrated to provide an improved picture of the viable amino acid sequence space of the protein. Because a typical protein design algorithm is, in a preferred embodiment, an integral feature of the present invention, the features of one typical protein design algorithm are described below. The algorithm, called SPA, comprises a series of steps as illustrated in FIG. 3, utilizing a scoring function, a genetic algorithm, amino acid reference energies, and a side chain module for selection of useful rotamer states.

Scoring Function and Geometries. In a preferred embodiment, the Amber potential energy function (Weiner et al., 1984) with the OPLS non-bonded parameters (Jorgensen & Tirado-Rives, 1988) is used as a basis for evaluation of the energies of protein models with different sequences and rotamer combinations. A preferred form of the potential includes most of the terms of the Amber potential: non-bonded, electrostatic, and torsional energies. Fixed bond lengths and angles (set at the equilibrium values described for the Amber force field) are used for side chain geometries, eliminating the need for bond stretching and angle bending terms. The energy (or score) of a model is therefore calculated as follows:

$$E = \sum_{torsions} \frac{V_n}{2} [1 + \cos(n\chi)] +$$
$$\sum_i \sum_{j>i} 4\varepsilon \left[ \left(\frac{\sigma}{R_{i,j}}\right)^{12} - \left(\frac{\sigma}{R_{i,j}}\right)^6 \right] +$$

-continued $$\frac{q_i q_j}{DR_{i,j}} + \sum_i S_i \Delta A_i + \sum_{x=1}^{20} n_x B_x$$

where $R_{ij}$ is the distance between atoms i and j; $\sigma$ and $\varepsilon$ are the Lennard-Jones parameters related to the radii and well depth, respectively. The first term is a sum over side chain dihedral angles; the second term is a sum of non-bonded (Lennard-Jones) interactions over all atom pairs (side chain-side chain and side chain-backbone); the third term is a sum of electrostatic interactions summed over all charged atom pairs. Scaling factors for the non-bonded and electrostatic terms, and combining rules are those defined for use of the OPLS parameter set. In the current version of the algorithm, backbone geometries are fixed, so backbone self-energy terms are not evaluated.

The fourth term is used to represent the solvation energetics of the system (Eisenberg & McLachlan, 1986). The solvation free energy of a model structure is determined by summing the products of the atomic solvation parameter and the estimated change in solvent accessible surface area for each atom in the model structure, where the change is relative to an estimate of the average exposure of that atom type in the unfolded state of the protein. The use of atomic solvation parameters is expected to provide an approximation of the true solvation free energy, and has been used effectively for protein design (Gordon et al., 1999). Furthermore, recent theoretical results indicate that despite its simplicity, it can largely reproduce the energetics calculated using more •sophisticated methods (Hendsch & Tidor, 1999). In a preferred embodiment, three solvation parameters are used, corresponding to the burial of polar atoms (N,O), the burial of nonpolar atoms (C), and the exposure of nonpolar atoms (C). The first two terms represent conventional use of atomic solvation parameters, relating to the free energy cost of desolvation of polar groups and the strength of the hydrophobic effect, respectively. In a preferred embodiment, the desolvation penalty for the burial of polar atoms is furthermore a function of the extent of participation of the polar atom in a hydrogen bond. In a preferred embodiment, this is assessed using the condition that the distance between the hydrogen atom and the acceptor atom is less than 2.5 Å, and if the following function has a value less than –0.3:

$$f(\theta, \phi) = \cos^2(\theta_{D,H,A}) \cos(\phi_{H,A,AA})$$

where D, H, and A refer to the donor, hydrogen, and acceptor atoms, respectively, and the AA refers to the acceptor antecedent atom. The final term of the solvation function, a penalty factor for exposure of nonpolar surface, has been applied successfully for designing proteins by Mayo and colleagues (Dahiyat et al., 1997b; Gordon et al., 1999), and may be considered to be both an implicit fold-specificity constraint and a solubility constraint.

In a preferred embodiment, the strengths of the solvation parameters are optimized by comparing the properties of designed protein sequences and natural protein statistics and changing the parameters such that the designed proteins have properties similar to natural proteins. This process is described in more detail below.

Amino Acid Reference Energies. A set of correction factors to account for changes in amino acid sequence within the design process has been generated. These factors account for the absence of an explicit reference state in the calculation of the energy of a designed sequence. The factors are referred to as amino acid reference energies or baseline corrections. In a preferred embodiment, the correction factors depend on composition only. In an alternative embodiment, the correction factors will depend furthermore on structural environment such as secondary structure class. The application of these 20 factors is straightforward, and is of the following form.

$$CC = \sum_{x=1}^{20} NC_{x,d}E_x$$

where $C_{x,d}$ is the fractional composition of amino acid type x in the designed sequence and N is the length of the sequence.

Side Chain Sampling and Optimization. A rotamer library of statistically prevalent combinations of side chain dihedral angles (Dunbrack & Cohen, 1997) is used to guide sampling of side chain identities and orientations in the combinatorial search for low energy structures. In a preferred embodiment, additional flexibility is incorporated by adding discrete or randomly chosen increments of +/-15□ to the first two dihedral angles of each library rotamer.

In the present invention, any heuristic or deterministic protein design algorithm (Desjarlais & Clarke, 1998) can be used for performing the combinatorial search of processing step 54. Heuristic methods include genetic algorithms (GA) (Desjarlais & Handel, 1995; Holland, 1992; Lazar et al., 1997) and Monte Carlo searches (Kuhlman & Baker, 2000; Voigt et al., 2000), while deterministic methods include DEE (Dahiyat & Mayo, 1996; Desmet et al., 1992) or Self-Consistent Mean Field Theory (Koehl & Delarue, 1996; Lee, 1994; Voigt et al., 2001).

The SPA utilizes a GA for the optimization, which is applied as outlined in FIG. 3. In a preferred embodiment, an initial population of 300 members is generated by creation of models with side chains at each position sampled randomly from the list of useful rotamers 42. This sampling is biased according to a Boltzmann probability of the rotamer—these probabilities define a selection matrix for the design procedure. In early cycles of the design procedure, the selection matrix can be derived from the side-chain backbone energies alone. In later rounds, the selection matrix can be extracted from the early rounds of the method (see below). The energy of each complete model in the population is calculated according to the scoring function described above. Based on these energies, selective recombination between models is performed. In a preferred embodiment, a uniform crossover scheme is used. Parent models are selected from a selection matrix weighted according to the Boltzmann probability of the model, calculated from its energy and a temperature that is set at each round according to a predefined diversity value. In a preferred embodiment, this value, defined as the informational entropy of the population, is set to decay linearly from 5.5 to 3.0 throughout the simulation. Finally a small amount of random mutation at a preferred frequency of 0.04 is used to modify the population generated by crossover of parent models. In a preferred embodiment, this cycle of energy evaluation, selective recombination, and mutagenesis is repeated at least 100 times. At the conclusion of the simulation, the sequence with the lowest total energy is taken as the designed sequence.

Defining Useful Rotamers. In a preferred embodiment of the invention, a rotamer library is pre-filtered for a given structural template to partially alleviate the enormous combinatorial complexity involved in protein sequence optimization. Filtering is based on steric and solvent effects. The steric filter is straightforward. For a given position, any rotamer that results in an energy of interaction with the backbone structure greater than 20 kcal/mol is rejected. The second filter is designed to prevent the burial of polar groups or the hyper-exposure of nonpolar groups. This filtering stage is performed as follows. Each possible side chain rotamer is placed into a position on the backbone structure. The extent of burial of each of its atoms is then assessed relative to a set of generic side chain centroid coordinates at all other positions, defined at 2.9 Å from the $C_\alpha$ atom along a standard geometry $C_\alpha$-$C_{\beta2}$ bond vector. A contact score for each rotamer atom is defined as (Micheletti et al., 1998):

$$C_a = \sum_{i=1}^{chainlength} \frac{1}{1+e^{d_{a,i}-6.5}}$$

where $C_a$ is the contact score for atom a, and $d_{a,i}$ is the distance between atom a and the side chain centroid at position i. Rotamers of side chains containing polar atoms {Asp, Glu, Lys, Asn, Gln, Arg, Ser, Thr, Tyr, Trp} are eliminated when any of their polar atoms have a contact score greater than 5.5 and are incapable of forming hydrogen bonds with the backbone. Rotamers of nonpolar side chains {Phe, Ile, Leu, Val, Pro, Trp} are eliminated when any of their atoms have a contact score less than 2.0. These criteria are defined conservatively because of the coarse nature of the definition of burial. Trp side chains are subject to both criteria. Ala and Gly residues are not subject to filtering. The filtered library is stored in memory 24 as a set of useful rotamers 42.

Other groups have used definitions of surface, buried, and boundary positions to generate position-specific subsets of amino acid types (Dahiyat & Mayo, 1997a; Dahiyat et al., 1997b). The approach described here obviates the need for explicit definition of burial class, in principle allowing appropriate subsets of rotamers from all amino acid types at some positions.

Mean Field/Ensemble-Averaged Protein Design

The central feature of the present invention is its use to define mean field probabilities or free energy values that represent the viable amino acid sequence space for a protein fold. In contrast to other approaches that yield mean field free energy estimates, this method can readily be applied to multiple backbone states, and does not require the use of a pairwise decomposable scoring function.

It should be emphasized that computational protein design procedures prior to the present invention deal almost exclusively with a fixed backbone structure for input, with few exceptions. The present invention, however, provides a strategy for incorporating information from an ensemble of related backbone structures, taking advantage of the greater diversity of amino acids encouraged by backbone flexibility, and accounting for physically realistic motions of the backbone.

The method approximates free energy values by expansion of states about multiple local minima converged to by a typical protein design algorithm (an algorithm which designs an amino acid sequence for a given backbone structure) (Raha et al., 2000). These local minima, or 'nucleated' states, are assumed to be representative of the most highly populated states of the system. It should be noted that the nucleated state created at step 54 of FIG. 2 can be provided by any protein design algorithm that yields a protein sequence and structure. Protein design algorithms include, but are not limited to, dead end elimination algorithm, genetic algorithm, Monte Carlo algorithm, self consistent mean field theory algorithm and the like, or combinations thereof. In an alternative embodiment, the nucleated state can be the full sequence and structure of a natural protein as in step 68, inclusive of all of the original side chains in their experimentally determined orientations. Within the context of each nucleated state, all amino acid types in all rotamer orientations (drawing from a rotamer library) are sampled and evaluated at step 56 for each position. The total energy of each sampled state is incorporated at step 60 into a running partition function, defined below, assigned to the amino acid/rotamer combination of interest. In a preferred embodiment, the total partition function $Q_{x,r,i}$ for each amino acid/rotamer, summed over multiple nucleated structures, is ultimately converted at step 62 directly into a mean field free energy value using a well known statistical mechanics relation. In a preferred embodiment, the method combines information derived by designing sequences for an ensemble of related backbone structures provided at step 50, such that the designed sequences correctly sample the provided degrees of freedom in backbone geometry. The advantage of the approach is significant: all amino acids at each position are evaluated multiple times with respect to many high probability environments.

In a preferred embodiment, the ensemble of related protein backbone structures provided at step 50 of FIG. 2 is generated (typically 100) from a high-resolution crystal structure, a high resolution NMR structure, or a high quality comparative model of a known protein. The individual backbone structures in the ensemble can be generated by Monte Carlo or molecular dynamics simulations, using well known methods. Alternatively, the backbone ensemble can be derived directly from an ensemble of experimentally determined NMR structures, a set of structures taken from distinct members of a protein family, or a set of structures determined separately for the same protein. For each individual structure, a protein design algorithm is applied at step 54 to generate a set of side chain identities and rotamer orientations that are optimal (or near optimal) for the structure. Each new structure/sequence combination is treated as a "nucleated state", and is taken to be representative of a high probability sequence/structure combination.

To determine the fitness of each amino acid/rotamer at a specific position in the context of the nucleated state, the side chain identities and rotamers at all other positions in the protein are frozen. The rotamers of all amino acid types are then sampled exhaustively (drawing from a rotamer library) at step 56 for the position of interest, and the energy of the corresponding model is evaluated according to the scoring function. The Boltzmann weight of each sampled side chain/rotamer is then added to an ongoing partition function as follows:

$$Q_{x,r,i} = \sum_{m=1}^{N} \sum_{s} e^{-\Delta E_{x,r,s,i,m}/RT}$$

Where x is the amino acid type, s is a sub-rotamer state of rotamer r of amino acid x, i is the position in the structure, m is the nucleated model, and N is the total number of models used. $E_{x,r,s,i,m}$ is the total calculated energy, according to the scoring function described above, of the nucleated model, given the current sub-rotamer of amino acid type x at position i. In a preferred embodiment, 15 sub-rotamer states within 20 degrees of the central rotamer state are sampled randomly. A set of partition functions $\{Q_{x,r,i}\}$ for all amino acid rotamers at all positions in the protein defines a probability matrix.

The partition function for each amino acid/rotamer combination is continually updated at step as more backbone structures and/or nucleated states are added to the simulation via the cycle between steps 52 and 58. Because each nucleated state contains a unique configuration of backbone structure, side chain identities, and rotamers, each rotamer state is exposed to a wide range of environments. In a preferred embodiment, application of said cycles would involve the selection of a new backbone structure for each cycle. It is generally found that the use of at least 30 cycles between steps 52 and 58 is sufficient to ensure statistical convergence, although in some cases fewer cycles will suffice. There is also generally a practical upper limit on the number of cycles that is dependent on time limitations imposed by the CPU of the computer.

The total partition function $Q_{x,r,i}$ for amino acid type x, in rotamer state r, at position i, evaluated over N model structures, can be converted to a Helmholtz free energy at step 62 using the equation below:

$$A_{x,r,i} = -RT \ln Q_{x,r,i}$$

where $A_{x,r,i}$ is the Helmholtz free energy of amino acid x in rotamer state r at position i. The temperature (T) in both equations can have a range of values and should be optimized for the application. Values ranging from 300 K to 3000 K have been used successfully.

In a preferred embodiment, at least two cycles between steps 50 and 60 are performed to ensure self-consistency in the final probability matrix and free energy values. In a preferred embodiment, the $Q_{x,r,i}$ values, representing the cumulative probability of each rotamer state, are used to guide the next cycle of design simulations by serving as a probabilistic selection matrix for amino acids and rotamers in step 54.

In an alternative embodiment, the partition functions for all rotamers of each amino acid at each position are added together to represent the total probability of the amino acid x at position i:

$$Q_{x,i} = \sum_{r} Q_{x,r,i}$$

In such cases, the Helmholtz free energy for each amino acid at each position is calculated as:

$$A_{x,i} = -RT \ln Q_{x,i} + T\Delta S_x$$

where $\Delta S_x$ represents an estimate of the configurational entropy of amino acid type x in an appropriate reference state.

In a preferred embodiment, the probability matrix defined by the set $\{Q_{x,r,i}\}$ or the free energy matrix defined by the set $\{A_{x,r,i}\}$ is utilized to design a single optimal protein sequence for the structure as in step 64 of FIG. 2. In a further aspect, the protein sequence can be physically produced in the laboratory by well known methods and characterized.

In an alternative preferred embodiment, the probability matrix or free energy matrix is utilized to guide the design of one or more combinatorial libraries of protein sequences, as in step 66 of FIG. 2. A combinatorial library is taken herein to mean a large set of protein sequences wherein each individual sequence is made up of some combination of amino acids as specified by construction of the library.

Because of the importance of combinatorial libraries to the general goal of producing proteins with altered or improved properties, the quality and nature of the probability or free energy matrix that is used to design the combinatorial libraries is of immense importance. The present invention produces a probability matrix that is superior in several aspects to matrices that can be derived by application of a typical protein design algorithm. A typical protein design algorithm can be encouraged to generate a crude probability matrix based on repeated application of the algorithm under different conditions (different backbones, different random number seeds, etc.), as in a cycle between steps 52 and 54 of FIG. 2. However, such a matrix will in most cases contain incomplete information: if an amino acid is never found at a particular position, the user does not know if the amino acid is not found because it is unfavorable, or if it simply has not occurred in a set number of repeated applications. Furthermore, the quantitative accuracy of the probability matrix derived in such a manner can be compromised by similar circumstances.

In contrast to these limitations, the present invention provides a quantitatively superior probability matrix. All amino acids are evaluated at every cycle of the program (step 56 of FIG. 2), within multiple contexts.

In certain circumstances, it may be desirable to predict the viable sequence space for a protein that is subject to multiple constraints. For example, some proteins function by adopting two distinct structural forms. Each form would give rise to its own probability matrix. In such cases, application of the present invention can be used to combine information from separate probability matrices such that a single probability matrix is defined that incorporates multiple constraints. In a preferred embodiment, the information is combined by adding or subtracting free energy matrices derived from the probability matrices. Furthermore, in a preferred embodiment, the combining process is applied iteratively to ensure proper convergence to a unified solution.

Parameterization of Scoring Functions and Simulation Variables

A central aspect of protein design algorithms is the choice of appropriate parameters for use in the energy/scoring function that determines the quality of a designed model. We have developed an approach for parameterizing protein design algorithms that incorporates statistical information from natural protein families. This approach represents an important departure from other methods that use limited experimental information to optimize parameters: because natural protein sequences are selected under multiple evolutionary constraints, the use of natural sequence statistics provides a comprehensive measure of the quality of a designed protein sequence, and by extension, a better measure of a parameter optimum.

Figure 4:
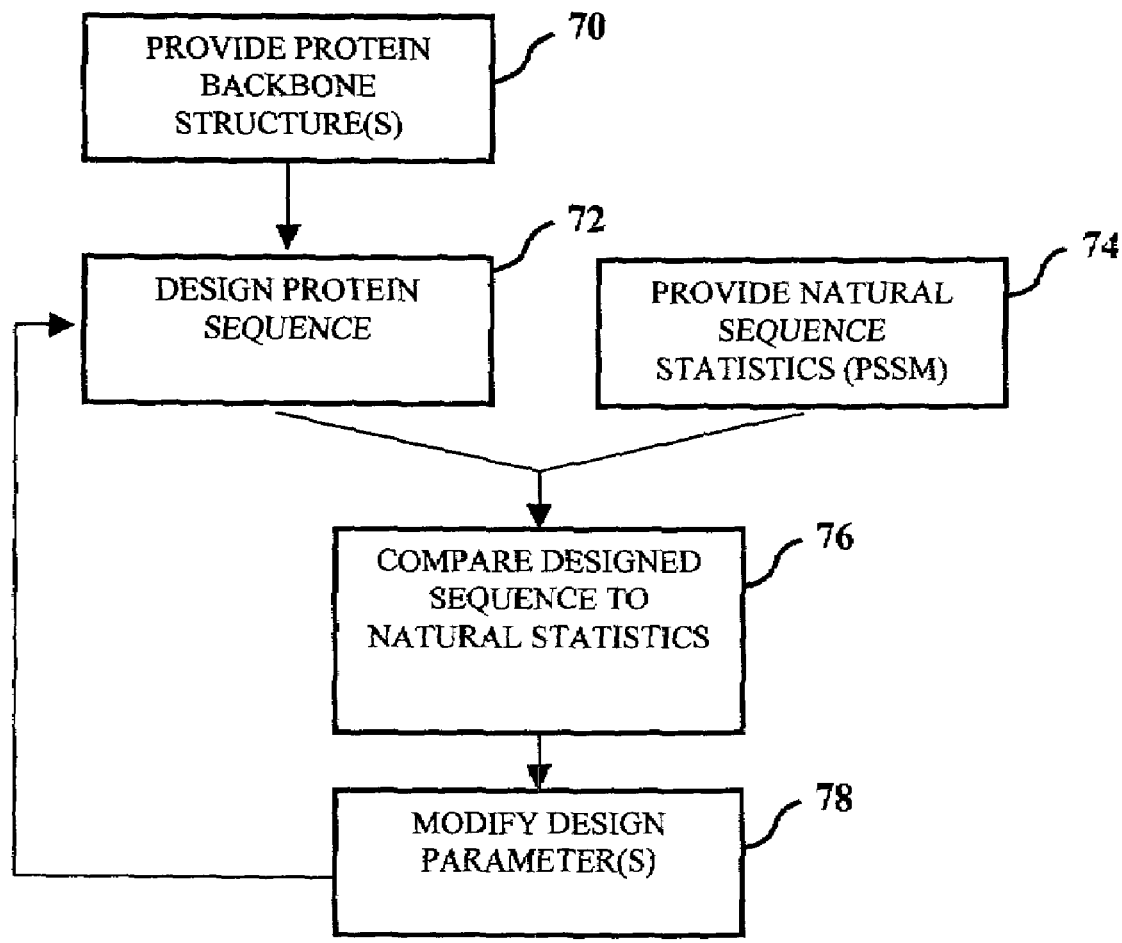
FIG. 4 illustrates a protein design parameterization cycle. Repeated application of a protein design algorithm and comparison of the designed proteins to natural sequences is used to optimize simulation parameters.

The current invention utilizes natural protein sequence statistics, in the form of position-specific scoring matrices, to quantitatively evaluate and optimize parameters for a scoring function. The method is also extremely useful for determining optimal parameters for other aspects of protein design simulations, such as the extent of diversity in side chain placement (rotamer orientations) or the extent of diversity in backbone structure when using an ensemble-based protein design method. The method can be appreciated more fully by reference to FIG. 4.

To apply the parameter optimization procedure, a natural protein structure 70, to be used as a training system, is chosen from the protein data bank (PDB). In a preferred embodiment, the protein is a member of a large and diverse family of proteins with related structures (for instance, SH3 domains, RRM domains, α-β-α domains β-barrel domains, SH2 domains, leucine zipper domains, zink finger kinase domains, etc.). Application of a protein design algorithm yields a designed protein sequence at step 72 of FIG. 4. The properties of the designed sequence are compared to natural protein statistics 74.

In a preferred embodiment, a multiple sequence alignment for the protein family is constructed using any of a number of available programs, including but not limited to ClustalW, HMMER, BLASTX and the like. Alternatively, a pre-existing alignment of the family is downloaded from a repository such as the Pfam database (http://pfam.wustl.edu/index.html). In a preferred embodiment, a position-specific scoring matrix (PSSM) made up of numerical elements $\{M_{x,i}\}$ where x is the amino acid type and i is the position in the alignment, is determined from the multiple sequence alignment. As will be appreciated by those in the art, this matrix is used to encode the average suitability of each amino acid type at each position of the structure by reporting the trends that were followed by nature. A total figure of merit F (often referred to as a profile score) for a designed sequence is taken as the sum of the $M_{x,i}$ values over the complete sequence $\{X_i, i=1,N\}$ of length N:

$$F = \sum_{i=1}^{N} M_{x,i}$$

In its simplest embodiment, the matrix will encode the frequencies $\{f_{x,i}\}$ or log frequencies $\{\log(f_{x,i})\}$ with which each of the twenty amino acid types occurs at each position in the alignment.

$$M_{x,i} = \log f_{x,i}$$

In a preferred embodiment, the PSSM is composed of the log-odds ratios for each of the amino acid types at each position. This ratio is defined as the log of the ratio of the position-specific frequency $f_{x,i}$, of each amino acid type at position i in the alignment, and its overall frequency of occurrence in all proteins $q_x$.

$$M_{x,i} = \log\left(\frac{f_{x,i}}{q_x}\right)$$

Note that if $f_{x,i}$ 32 0, then $f_{x,i}$ is artificially set to a small positive constant (such as 0.001) to avoid issues with the log factor. In a preferred embodiment, sequence-weighting procedures (Henikoff & Henikoff, 1994) are used to adjust the frequencies in the alignment to more accurately represent the diversity of the family.

A protein design algorithm is applied to generate an optimal or near-optimal sequence or set of sequences for the target (training) protein, using a starting set of parameters. The parameter to be optimized is systematically varied at step 78 of FIG. 4. For each new value of the parameter, a new designed sequence is generated at step 72, and evaluated by the function F at step 76. The optimal value of the parameter is thus estimated as that which yields the optimal value of F. In an alternative procedure, several parameters are simultaneously optimized by a steepest descents or conjugate gradient procedure. In this procedure, all parameters will be adjusted simultaneously in the direction of maximal increase in the F score, determined numerically by small perturbations of each individual parameter. Finally, in order to ensure generality of the parameters, a number of training proteins (and families) are used to derive parameters that yield the best average set of parameters for the algorithm.

For design simulations such as mean field methods, ensemble-based calculations, or methods that estimate amino acid probabilities by monte carlo methods, the parameterization method can also be applied. In such cases, the figure of merit will be a weighted average of the log-odds scores according to the ensemble probabilities. If $\{p_{x,i}\}$ represents a matrix of amino acid probabilities calculated from the simulation(s), then the ensemble averaged figure of merit is given by:

$$\langle F \rangle = \sum_{i=1}^{N} \sum_{x=1}^{20} p_{x,i} \log\left(\frac{f_{x,i}}{q_{x,i}}\right)$$

Estimation of Amino Acid Reference Energies. A key set of parameters for protein design are terms that represents the intrinsic energetic cost of placing a given amino acid type at any position in the protein, regardless of the environment. These terms have also been referred to as "baseline corrections". We have developed a method for derivation of a set of twenty reference values using natural sequence information. The resulting values are general, in the sense that they can be applied to a variety of protein motifs.

A set $\{E_x\}$ of 20 amino acid reference energies can be added to a protein design scoring function directly as the summation:

$$CC = \sum_{x=1}^{20} N C_{x,d} E_x$$

where $C_{x,d}$ is the fractional composition of amino acid type x in the designed sequence and N is the length of the sequence. Derivation of amino acid reference energies is based on the assumption that the optimal set of values is that which, when included in the scoring function of a protein design algorithm, yields the most correct designed compositions for a set of target backbone structures. The definition of correct can have several meanings, as discussed below.

Assuming that the "correct" target composition $\{C_{x,t}\}$ is predefined, reference values are iteratively optimized by comparing the compositions of designed sequences to target sequences. First, a protein design algorithm is applied to generate an optimal or near-optimal sequence for a target (training) protein, using a starting set of reference energies (typically zero for the first round of iteration). Next, the composition of the designed sequence $\{C_{x,d}\}$ is calculated from the final output of the simulation and quantitatively compared to the target composition $\{C_{x,t}\}$ to yield a correction factor for each reference energy.

$$correction_x = b \log\left(\frac{C_{x,d}}{C_{x,t}}\right)$$

where b is a parameter that determines the rate of training. The correction factor derived for a given round of iteration is added to the previous value of the reference energy to yield an updated value of the reference energy, $$E_{x,k} = E_{x,k-1} + b \log\left(\frac{C_{x,d}}{C_{x,t}}\right)$$

where $E_{x,k}$ is the value of the reference energy $E_x$ for the kth round of training. The mechanism of the correction factor should be clear: if the design algorithm incorporates an excessive amount of amino acid type x, the reference energy $E_x$ for that amino acid is increased incrementally.

Because of the log factor in the correction term, a few special conditions are required for cases in which either $C_{x,d}$ or $C_{x,t}$ is zero. (a) If $C_{x,d}=0$, then a simple constant correction term (e.g. −0.1 kcal/mol) is applied to favor the incorporation of amino acid type x in designed sequences. (b) If $C_{x,t}=0$, $C_{x,t}$ is artificially set equal to 0.01 (or some other small factor). In a preferred embodiment, a condition is set so that if the $C_{x,d}$ and $C_{x,t}$ differ by a preset small amount, no correction is made. This ensures stable convergence to a final set of reference energies The preceding steps are repeated until a converged set of parameters are defined. In a preferred embodiment, the whole procedure is repeated for a number of training proteins. This is done to ensure that the final reference energy values are robust and generally applicable. The average values of the reference energies derived from all training proteins serve as the final values. In an alternative embodiment, separate values of reference energies are derived for different classes of structure by clustering the proteins according to commonalities such as secondary structural class.

Several definitions of a correct target composition are possible. In a preferred embodiment, the target composition is equal to the composition of the single native sequence of the protein from which the training structure was derived.

EXAMPLES

Example 1

Protein Design Using Ensemble Averaging and Mean Field Free Energies

The most direct application of the invention is the design of a single protein sequence with the goal that the sequence, when produced experimentally, spontaneously adopts the target three-dimensional structure. To illustrate this process, the small protein motif typical of proteins in the WW family of protein domains was taken as a target structure.

In a preferred embodiment of the invention, the ensemble-averaging/mean field method utilizes a set of structurally similar protein backbones as input for the design process. In this manner, the degrees of freedom that are physically expected of a backbone can be taken into account directly. Furthermore, the extent of flexibility allowed in such a backbone can be explored to generate different results. In the present example, the ensemble of backbones was generated by a Monte Carlo procedure. Beginning with a single backbone structure taken from published coordinates of the Pin1 protein (Ranganathan et al., 1997), the Monte Carlo procedure, which operated by perturbing the backbone dihedral angles, was applied repeatedly to generate a series of backbone structures that had a root mean squared deviation from the original structure of 0.3 angstroms. Because of the stochastic nature of the Monte Carlo procedure, each of the resultant backbone structures is unique.

Figure 5:
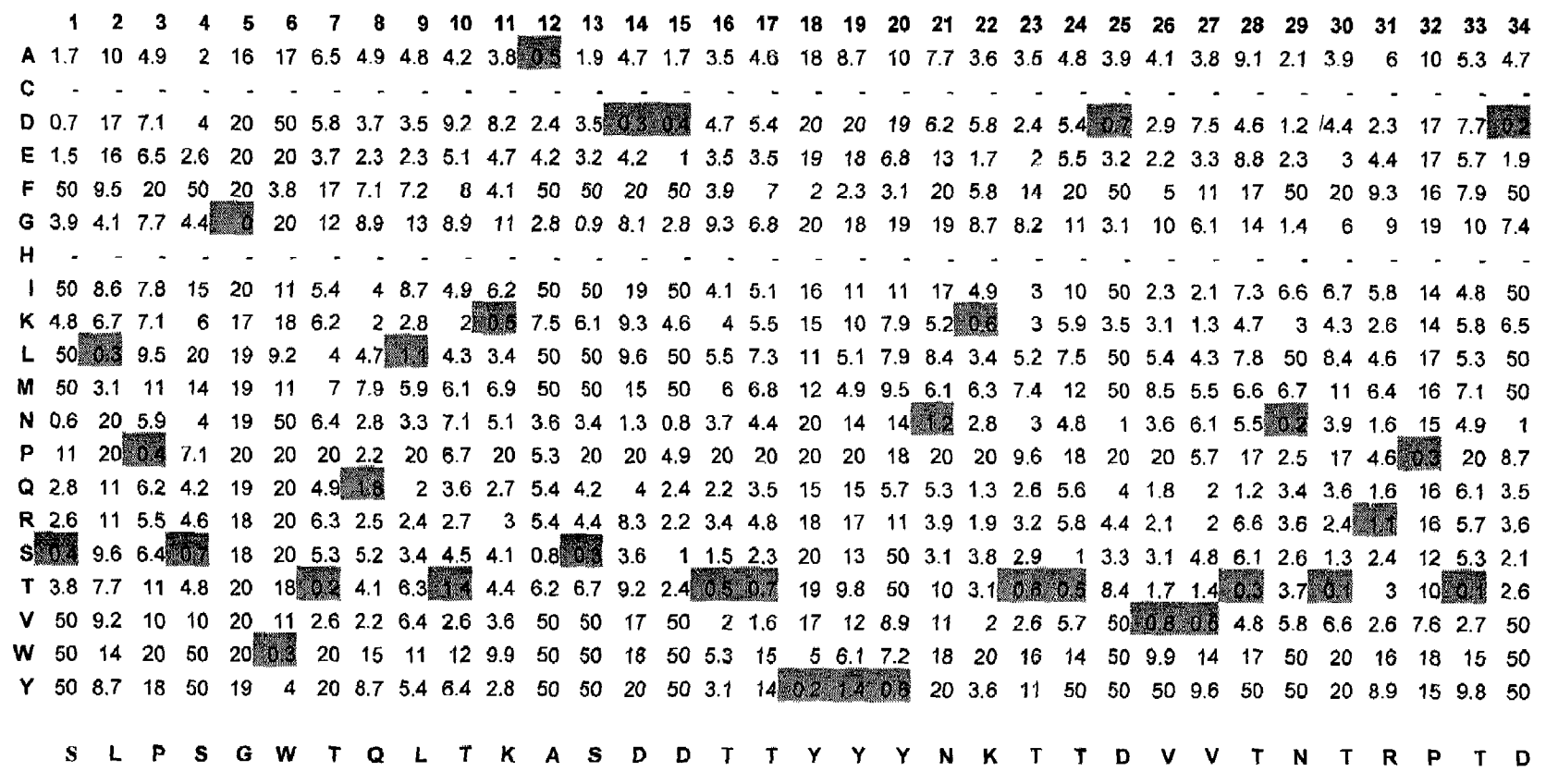

The ensemble averaging/mean field method, as outlined in FIG. 2, was applied to the input backbone ensemble to determine a mean field free energy matrix representing the suitability of all amino acids (excluding Cysteine and Histidine) and rotamer states at all positions in the structure. As is known in the art, a lower free energy value represents a higher suitability of the given amino acid/rotamer combination. The SPA program and scoring function, as highlighted above, was used for the design and all evaluation steps. For each major cycle of the procedure (represented by cycle/in FIG. 2), results from 30 representative backbone structures (m cycle in FIG. 2) were thermodynamically averaged to yield a final free energy matrix. Three major cycles were performed to ensure self-consistency in the results. A portion of the final free energy matrix, representing the lowest free energy rotamer state of each amino acid type at all positions, is shown in FIG. 5.

The free energy matrix can be utilized in a number of ways. In the present example, the matrix is used to choose a single protein sequence for production in the laboratory. Hence, the amino acid with the lowest free energy value at each position in the structure is used to design the protein.

A designed WW protein, consisting of 34 optimal amino acids from the final free energy matrix of FIG. 5, was produced in the laboratory using well-known methods, as follows. First, a set of overlapping synthetic DNA oligonucleotides encoding the designed protein were ordered from a commercial provider and purified by polyacrylamide gel electrophoresis. These oligonucleotides were assembled, again using well-known methods, as a fusion with a gene that encodes the N-terminal domain of calmodulin (N-cam), which acts as a convenient fusion partner for expression and purification of the desired protein. Any number of useful reporter proteins or purification tags, including but not limited to epitope tags, fluorescent proteins such as gfp could also be used as fusion partners. The N-cam-WW protein fusion was expressed in *E. coli* bacterial cells using well-known methods and subsequently purified by phenyl-sepharose chromatography. The purified fusion protein was then cleaved by the NIa protease to yield the designed WW domain, which was then further purified by high performance liquid chromatography.

Figure 6:
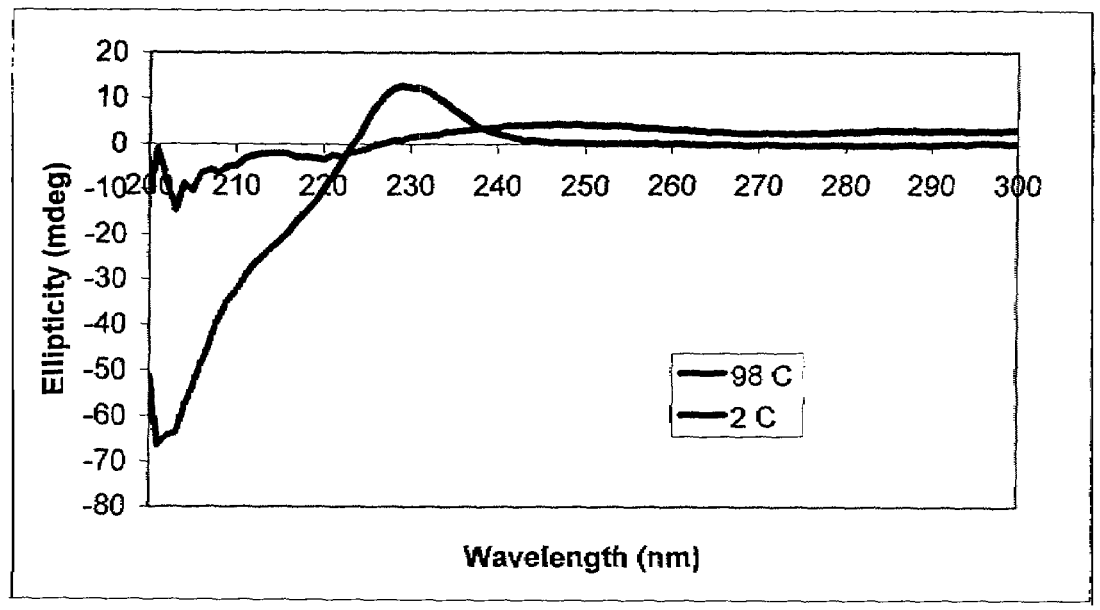
FIG. 6 shows circular dichroism (CD) spectra for the designed WW domain discussed in Example 1. Spectra were collected at 2° C. and 98° C.
Figure 7:
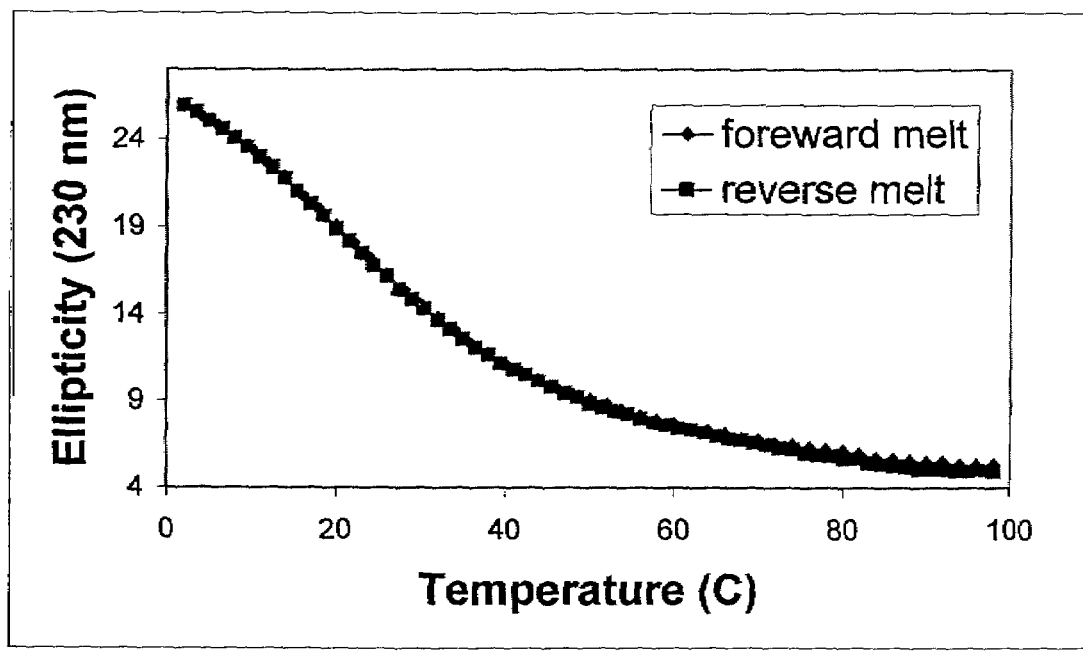
FIG. 7 shows a thermal denaturation of the designed WW domain monitored by CD.

The purified form of the designed WW domain was characterized by Circular Dichroism (CD) spectroscopy. FIG. 6 shows CD spectra collected for the designed WW protein at 2° C. and 98° C. The spectra reveal that at lower temperatures, the protein is folded into a structure that is related to the target structure, judging from the fact that the positive peak observed in the low temperature spectrum at approximately 230 nm is also observed in the natural protein (not shown). While the true structure cannot be directly known without further experimental characterization, those in the art will appreciate that a positive CD signal at 230 nm is rare for proteins, and that its existence in the spectrum of the designed protein is compelling evidence of structural similarity to the target.

A thermal denaturation of the designed WW domain was also performed while monitoring the CD signal at 230 nm. A clear sigmoidal transition from folded to unfolded protein is observed. Furthermore, a thermal renaturation experiment over the same temperature range yields identical behavior. As is known in the art, these behaviors are consistent with a cooperatively folded protein domain.

In summary, these sets of data strongly suggest that the new WW domain protein designed using the invention spontaneously adopts the desired three-dimensional structure, and has properties expected of a natural protein. As will be appreciated by those in the art, this designed protein represents one of a very small number of proteins that have been successfully designed by a fully automated protein design procedure. As will also be appreciated in the art, this protein is composed predominantly of β-sheet secondary structure, a type of structure that has proven difficult to design successfully.

Example 2

Designing Combinatorial Libraries of Proteins

An important extension of protein design algorithms is their use to guide the rational design and construction of combinatorial libraries. Such libraries can be produced genetically in the laboratory, then screened or selected for desired properties as previously described herein. Desired properties can include, but are not limited to, enhanced catalytic activity, improved stability, altered specificity, and enhanced activity/stability under extreme conditions. Alternatively in certain circumstances, it may be desired to remove or attenuate a selected protein function (i.e., enzymatic activity etc.) which can be effected by appropriate protein design as described herein. Combinatorial libraries and the molecular diversity they represent are of extreme importance in the biotechnology arena. However, their use has not been explored in depth, so an ability to control the extent and type of diversity encoded by a library is paramount to further developments in the field.

A unique feature of a complete mean field free energy matrix is the ability to control the extent and type of diversity of a corresponding combinatorial library. The simplest method for library design is to slowly increase an upper limit on the allowed free energy scale, incorporating any amino acids that fall within the allowed range into the combinatorial library. Once the desired level of complexity is achieved, the procedure is stopped. The complexity of a library is defined simply as the product of the number of amino acids allowed at each position of the structure. FIG. 8A shows a combinatorial library constructed for the WW motif, using the free energy matrix that was derived in Example 1, and the simple free energy scaling method. The library was constructed to have a complexity of approximately $10^5$. To illustrate the flexibility of options available when a complete free energy matrix exists, the complexity of the library is increased further by simply raising the upper limit on free energy, as in FIG. 8B, where the combinatorial library is constructed to have a complexity of approximately $10^8$.

An alternative procedure to the construction of combinatorial libraries is to slowly decrease a lower limit on the normalized probability of each amino acid at each position in the structure. As is known in the art, the normalized probability $P_{x,i}$ of amino acid type x at position i can be related directly to the free energy $A_{x,i}$ by the relationship $$p_{x,i} = \frac{e^{-A_{x,i}/RT}}{\sum_{x=1}^{20} e^{-A_{x,i}/RT}}$$

FIG. 8C shows a combinatorial library designed using a procedure in which amino acids are incorporated into the library at incrementally lower probability, beginning with the highest probability amino acids at each position (corresponding to the sequence characterized in Example 1). The procedure was ceased when a complexity of $10^5$ was achieved, so that the library can be compared directly to that in FIG. 8A. Importantly, the nature of the two libraries are significantly different. For instance, note that the latter procedure results in a more even distribution of the complexity throughout the protein, whereas the former procedure focuses the diversity at a smaller number of positions. It should be emphasized that it is presently unknown which type of library will lead to more successful production of proteins in the laboratory. It is likely that different procedures such as those highlighted here will find optimal use in different applications.

It should be understood that this level of control over combinatorial library design far exceeds that obtained by application of a typical protein design algorithm. Table 1 shows a comparison between a probability matrix derived by repeated application of the SPA program as outlined in FIG. 3 and a probability matrix derived in accordance with the present invention as outlined in FIG. 2. In the former case, a simple list of amino acid frequencies of occurrence would be created. This list would constitute an incomplete view (question marks in Table 1) of the diversity of amino acids that are allowed for the structure. For example, multiple applications of a typical protein design algorithm suggest that a Thr at position 7 is very likely, and that the suitability of Val at the same position is unknown. However, the present invention reveals that Val, while less probable than Thr, should be considered seriously for incorporation into a combinatorial library.

Throughout the present disclosure, references are made to various publications, the complete titles and citations of which are appended herewith, all of which are hereby incorporated by reference in their entirety.

Although the invention describes in detail certain embodiments, it is understood that variations and modifications exist which are within the scope of the invention as set forth in the following claims.

References Cited

Dahiyat, B. I., Gordon, D. B. & Mayo, S. L. (1997a). Automated design of the surface positions of protein helices. *Protein Sci* 6(6), 1333-7.

Dahiyat, B. I. & Mayo, S. L. (1996). Protein Design Automation. *Protein Science* 5, 895-903.

Dahiyat, B. I. & Mayo, S. L. (1997a). De novo protein design: fully automated sequence selection. *Science* 278 (5335), 82-7.

Dahiyat, B. I. & Mayo, S. L. (1997b). Probing the role of packing specificity in protein design. *Proc Natl Acad Sci USA* 94(19), 10172-7.

Dahiyat, B. I., Sarisky, C. A. & Mayo, S. L. (1997b). De novo protein design: towards fully automated sequence selection. *J Mol Biol* 273(4), 789-96.

Delarue, M. & Koehl, P. (1997). The inverse protein folding problem: self consistent mean field optimization of a structure specific mutation matrix. *Pac Symp Biocomput*, 109-21.

Desjarlais, J. R. & Clarke, N. D. (1998). Computer search algorithms in protein modification and design. *Curr Opin Struct Biol* 8(4), 471-5.

Desjarlais, J. R. & Handel, T. M. (1995). De novo design of the hydrophobic cores of proteins. *Protein Science* 4, 2006-2018.

Desjarlais, J. R. & Handel, T. M. (1999). Side-chain and backbone flexibility in protein core design. *J Mol Biol* 290(1), 305-18.

Desmet, J., De Maeyer, M., Hazes, B. & Lasters, I. (1992). The dead-end elimination theorem and its use in protein side-chain positioning. *Nature* 356(9), 539-542.

TABLE 1

|  | multiple sequence design[a] | | | | | | | | present invention[b] | | | | | | | |
| --- | --- | --- | --- | --- | --- | --- | --- | --- | --- | --- | --- | --- | --- | --- | --- | --- |
|  | 1 | 2 | 3 | 4 | 5 | 6 | 7 | 8 | 1 | 2 | 3 | 4 | 5 | 6 | 7 | 8 |
| Ala | 3 | ? | 15 | ? | ? | ? | ? | 6 | 10.5 | 0.4 | 6.8 | 17.3 | 0.0 | 0.0 | 2.0 | 2.8 |
| Asp | 39 | ? | ? | 11 | ? | ? | ? | ? | 17.3 | 0.0 | 2.3 | 6.4 | 0.0 | 0.0 | 2.8 | 5.2 |
| Glu | 2 | ? | ? | 1 | ? | ? | 8 | 16 | 11.6 | 0.0 | 3.1 | 12.8 | 0.0 | 0.0 | 8.1 | 10.4 |
| Phe | ? | ? | ? | ? | ? | 6 | 1 | 3 | 0.0 | 0.7 | 0.0 | 0.0 | 0.0 | 12.8 | 0.0 | 0.9 |
| Gly | ? | 33 | ? | ? | 100 | ? | ? | ? | 3.5 | 9.7 | 1.7 | 5.2 | 99.8 | 0.0 | 0.2 | 0.4 |
| Ile | ? | ? | ? | ? | ? | 2 | ? | ? | 0.0 | 1.0 | 1.6 | 0.0 | 0.0 | 0.4 | 3.4 | 4.5 |
| Lys | ? | ? | ? | ? | ? | ? | 1 | 12 | 2.2 | 2.6 | 2.3 | 2.3 | 0.0 | 0.0 | 2.3 | 12.1 |
| Leu | ? | 62 | ? | ? | ? | 7 | ? | 2 | 0.0 | 64.8 | 0.7 | 0.0 | 0.0 | 0.9 | 6.9 | 3.1 |
| Met | ? | 3 | ? | ? | ? | ? | ? | ? | 0.0 | 16.0 | 0.3 | 0.1 | 0.0 | 0.4 | 1.5 | 0.6 |
| Asn | 18 | ? | 1 | ? | ? | ? | ? | 2 | 18.2 | 0.0 | 4.1 | 6.4 | 0.0 | 0.0 | 2.1 | 8.1 |
| Pro | ? | ? | 81 | ? | ? | ? | ? | 20 | 0.1 | 0.0 | 64.5 | 1.4 | 0.0 | 0.0 | 0.0 | 10.9 |
| Gln | ? | ? | ? | ? | ? | ? | ? | 11 | 6.1 | 0.4 | 3.6 | 5.8 | 0.0 | 0.0 | 4.4 | 13.4 |
| Arg | ? | ? | ? | ? | ? | ? | ? | 16 | 6.7 | 0.4 | 5.0 | 4.7 | 0.0 | 0.0 | 2.2 | 9.4 |
| Ser | 37 | 1 | 3 | 88 | ? | ? | ? | 1 | 20.1 | 0.6 | 3.2 | 33.1 | 0.0 | 0.0 | 3.6 | 2.4 |
| Thr | ? | ? | ? | ? | ? | ? | 90 | ? | 3.7 | 1.6 | 0.4 | 4.3 | 0.0 | 0.0 | 46.4 | 4.2 |
| Val | ? | ? | ? | ? | ? | 2 | ? | 6 | 0.0 | 0.8 | 0.5 | 0.3 | 0.0 | 0.3 | 14.0 | 10.9 |
| Trp | ? | ? | ? | ? | ? | 65 | ? | ? | 0.0 | 0.1 | 0.0 | 0.0 | 0.0 | 73.6 | 0.0 | 0.0 |
| Tyr | ? | 1 | ? | ? | ? | 18 | ? | 4 | 0.0 | 1.0 | 0.0 | 0.0 | 0.0 | 11.6 | 0.0 | 0.4 |

[a]Amino acid incorporation statistics from 90 applications of the SPA protein design program;
[b]Probability matrix derived by application of the present invention Dunbrack, R. L., Jr. & Cohen, F. E. (1997). Bayesian statistical analysis of protein side-chain rotamer preferences. *Protein Sci* 6(8), 1661-81.

Eisenberg, D. & McLachlan, A. D. (1986). Solvation energy in protein folding and binding. *Nature* 319(6050), 199-203.

Goldstein, R. F. (1994). Efficient rotamer elimination applied to protein side-chains and related spin glasses. *Biophys J* 66(5), 1335-40.

Gordon, D. B., Marshall, S. A. & Mayo, S. L. (1999). Energy functions for protein design. *Curr Opin Struct Biol* 9(4), 509-13.

Harbury, P. B., Tidor, B. & Kim, P. S. (1995). Repacking protein cores with backbone freedom: structure prediction for coiled coils. *Proc Natl Acad Sci USA* 92(18), 8408-12.

Hellinga, H. W. (1997). Rational protein design: combining theory and experiment. *Proc Natl Acad Sci USA* 94(19), 10015-7.

Hellinga, H. W. & Richards, F. M. (1994). Optimal sequence selection in proteins of known structure by simulated evolution. *Proc Natl Acad Sci USA* 91(13), 5803-7.

Hendsch, Z. S. & Tidor, B. (1999). Electrostatic interactions in the GCN4 leucine zipper: substantial contributions arise from intramolecular interactions enhanced on binding. *Protein Sci* 8(7), 1381-92.

Henikoff, S. & Henikoff, J. G. (1994). Position-based sequence weights. *J Mol Biol* 243(4), 574-8.

Holland, J. H. (1992). *Adaptation in natural and artificial systems*, The MIT Press, Cambridge, Mass.

Johnson, E. C., Lazar, G. A., Desjarlais, J. R. & Handel, T. M. (1999). Solution structure and dynamics of a designed hydrophobic core variant of ubiquitin. *Structure Fold Des* 7(8), 967-76.

Jorgensen, W. L. & Tirado-Rives, J. (1988). The OPLS potential functions for proteins. Energy minimizations for crystals of cyclic peptides and crambin. *Journal of the American Chemical Society* 110(6), 1657-1666.

Koehl, P. & Delarue, M. (1994). Application of a self-consistent mean field theory to predict protein side-chains conformation and estimate their conformational entropy. *J Mol Biol* 239(2), 249-75.

Koehl, P. & Delarue, M. (1996). Mean-field minimization methods for biological macromolecules. *Curr Opin Struct Biol* 6(2), 222-6.

Kono, H. & Doi, J. (1994). Energy minimization method using automata network for sequence and side-chain conformation prediction from given backbone geometry. *Proteins* 19(3), 244-255.

Kono, H., Nishiyama, M., Tanokura, M. & Doi, J. (1998). Designing the hydrophobic core of Thermus flavus malate dehydrogenase based on side-chain packing. *Protein Eng* 11(1), 47-52.

Kuhlman, B. & Baker, D. (2000). Native protein sequences are close to optimal for their structures. *Proc Natl Acad Sci USA* 97(19), 10383-8.

Lazar, G. A., Desjarlais, J. R. & Handel, T. M. (1997). De novo design of the hydrophobic core of ubiquitin. *Protein Sci* 6(6), 1167-78.

Lazar, G. A., Johnson, E. C., Desjarlais, J. R. & Handel, T. M. (1999). Rotamer strain as a determinant of protein structural specificity. *Protein Sci* 8(12), 2598-610.

Lee, C. (1994). Predicting protein mutant energetics by self-consistent ensemble optimization. *J Mol Biol* 236(3), 918-39.

Micheletti, C., Seno, F., Maritan, A. & Banavar, J. R. (1998). Design of proteins with hydrophobic and polar amino acids. *Proteins* 32(1), 80-7.

Raha, K., Wollacoft, A. M., Italia, M. J. & Desjarlais, J. R. (2000).

Prediction of amino acid sequence from structure. *Protein Sci* 9(6), 1106-19.

Ranganathan, R., Lu, K. P., Hunter, T. & Noel, J. P. (1997). Structural and functional analysis of the mitotic rotamase Pin1 suggests substrate recognition is phosphorylation dependent. *Cell* 89(6), 875-86.

Street, A. G. & Mayo, S. L. (1999). Computational protein design. *Structure Fold Des* 7(5), R105-9.

Su, A. & Mayo, S. L. (1997). Coupling backbone flexibility and amino acid sequence selection in protein design. *Protein Sci* 6(8), 1701-7.

Voigt, C. A., Gordon, D. B. & Mayo, S. L. (2000). Trading accuracy for speed: A quantitative comparison of search algorithms in protein sequence design. *J Mol Biol* 299(3), 789-803.

Voigt, C. A., Mayo, S. L., Arnold, F. H. & Wang, Z. G. (2001). Computational method to reduce the search space for directed protein evolution. *Proc Natl Acad Sci USA* 98(7), 3778-83.

Weiner, S. J., Kollman, P. A., Case, D. A., Singh, U. C., Ghio, C., Alagona, G., Profeta, S. & Weiner, P. (1984). A new force field for molecular mechanical simulation of nucleic acids and proteins. *Journal of the American Chemical Society* 106(3), 765-784.

I claim:

1. A method exceucted by a computer under the control of a program, said computer including a memory for storing said program, said method comprising the steps of:
   providing an ensemble of related protein backbone structures;
   selecting a plurality of variable positions in said ensemble of related protein backbone structures;
   selecting a set of amino acids to computationally test at each of said variable positions in said backbone structures;
   applying to each protein backbone structure in said ensemble of related protein backbone structures a protein design algorithm to generate at least one variant protein sequence for each of said protein backbone structures;
   sampling each amino acid in said set of amino acids at each variable position in each variant protein sequence;
   evaluating the energetic fitness of each amino acid in said set of amino acids at each of said variable positions in each of said variant protein sequences for each of said protein backbone structures in said ensemble of related protein backbone structures;
   generating a probability matrix by combining said energetic fitness of each of said amino acids in each of said variant protein sequences for each of said protein backbone structures in said ensemble of related protein backbone structures to generate a total probability for each of said amino acids; and
   generating a combinatorial library of proteins from said probability matrix; and
   generating an output of the combinatorial library.

2. The method according to claim 1 wherein the step of sampling and evaluating fitness of one or more amino acids comprises sampling and evaluating fitness of different rotamers of the one or more amino acids at position in at least one backbone structure.

3. The method according to claim 1 that comprises selecting said variant protein sequences for the combinatorial library of proteins by identifying the amino acid with the lowest free energy at each position from the probability matrix.

4. The method according claim 1 wherein the step of evaluating energetic fitness comprises selecting an upper limit on free energy, and the step of generating said probability matrix comprises allowing amino acid variations among amino acids that are above the upper free energy limit.

5. The method according to claim 1 further comprising incorporating amino acids in the probability matrix generating step at incrementally lower probabilities until a desired complexity is achieved in the probability matrix, and generating a said combinatorial library of proteins from said probability matrix.

6. The method of claim 1 wherein the sampling an amino acid position comprises freezing side chain identities and rotamers at positions in the protein other than the sampled amino acid position.

7. The method according to claim 1 further comprising expressing the probability matrix as a set of partition functions.

8. The method according to claim 1 further comprising expressing the probability matrix as a free energy value.

9. The method of according to claim 1 wherein the probability matrix comprises information for all twenty amino acids.

10. The method according to claim 1 wherein the said steps of selecting a plurality of variable positions, selecting a set of amino acids, applying, sampling and evaluating are repeated more than once to generate said probability matrix.

11. The method according to claim 10 comprising in a subsequent repeat, using the probability matrix from a previous repeat.

12. The method according to claim 1 wherein said protein design algorithm comprises an optimization procedure selected from the group of: dead end elimination algorithm; genetic algorithm; Monte Carlo algorithm; and self consistent mean field theory algorithm or combination thereof.

13. The method according to claim 1 wherein at least one backbone structure of the ensemble is derived from the structure of a natural protein.

14. The method according to claim 1 wherein at least one backbone structure of the ensemble is generated by comparative modeling.

15. The method according to claim 1 wherein said ensemble of related backbone structures comprises backbone structures of a family of natural proteins.

16. The method according to claim 1 wherein said ensemble of related backbone structures is derived from an NMR structure.

17. The method according to claim 1 wherein said ensemble of related protein backbone structures is generated by a Monte Carlo simulation.

18. The method according to claim 1 wherein said ensemble of related protein backbone structures is generated by a molecular dynamics simulation.

19. The method according to claim 1 further comprising combining the information from at least two probability matrices to satisfy at least two constraints on sequence space.

20. The method according to claim 19 wherein the at least two constraints comprise a first constraint corresponding to a first structural form and second constraint corresponding to a second structural form that is distinct from the first structural form.

21. The method according to claim 19 comprising combining the at least two probability matrices by adding or subtracting free energies values from said probability matrices.

22. The method according to claim 19 wherein the step of combining information is repeated.

23. A method of providing a protein library, the method comprising:
   providing an ensemble of related protein backbone structures;
   selecting a plurality of variable positions in said ensemble of related protein backbone structures;
   selecting a set of amino acids to computationally test at each of said variable positions in said backbone structures;
   applying to each protein backbone structure in said ensemble of related protein backbone structures a protein design algorithm to generate at least one variant protein sequence for each of said protein backbone structures;
   sampling each amino acid in said set of amino acids at each variable position in each variant protein sequence;
   evaluating the energetic fitness of each amino acid in said set of amino acids at each of said variable positions in each of said variant protein sequences for each of said protein backbone structures in said ensemble of related protein backbone structures;

generating a probability matrix by combining said energetic fitness of each of said amino acids in each of said variant protein sequences for each of said protein backbone structures in said ensemble of related protein backbone structures to generate a total probability for each of said amino acids; and producing a library of proteins that include proteins that each comprise a sequence based on said probability matrix.

24. The method according to claim 23 further comprising screening or selecting one or more proteins from the library of proteins for a desired property.

25. The method of claim 24 wherein the screening or selecting one or more proteins from the library of proteins comprises identifying a protein with enhanced catalytic activity or altered specificity, relative to an initial protein whose backbone structure is one of the backbone structures of the ensemble.

* * * * *

UNITED STATES PATENT AND TRADEMARK OFFICE
CERTIFICATE OF CORRECTION

| | | |
|---|---|---|
| PATENT NO. | : 7,231,328 B2 | Page 1 of 1 |
| APPLICATION NO. | : 09/877695 | |
| DATED | : June 12, 2007 | |
| INVENTOR(S) | : John R. Desjarlais | |

It is certified that error appears in the above-identified patent and that said Letters Patent is hereby corrected as shown below:

In the Specification

At column 1, line 12, please delete "Provisional Patent Application" and insert -- invention --

At column 1, line 13, please delete "grant number CHE-9876234 from" and insert -- Grant No. CHE9876234, awarded by --

At column 1, lines 14-15, please delete "Accordingly, the U.S. government" and insert -- The Government --

Signed and Sealed this
First Day of July, 2014

Michelle K. Lee
*Deputy Director of the United States Patent and Trademark Office*

SEQUENCE LISTING

```
<160> NUMBER OF SEQ ID NOS: 4

<210> SEQ ID NO 1
<211> LENGTH: 34
<212> TYPE: PRT
<213> ORGANISM: Artificial Sequence
<220> FEATURE:
<223> OTHER INFORMATION: exemplary motif

<400> SEQUENCE: 1

Ser Leu Pro Ser Gly Trp Thr Gln Leu Thr Lys Ala Ser Asp Asp Thr
1               5                   10                  15

Thr Tyr Tyr Tyr Asn Lys Thr Thr Asp Val Val Thr Asn Thr Arg Pro
```

```
                    20              25              30
Thr Asp

<210> SEQ ID NO 2
<211> LENGTH: 34
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 1
<223> OTHER INFORMATION: Xaa = Ser, Asn, or Asp
<220> FEATURE:
<221> NAME/KEY: VARIANT
<222> LOCATION: 8
<223> OTHER INFORMATION: Xaa = Gln, Lys, Pro, Val, Glu, or Arg
<220> FEATURE:
<221> NAME/KEY: VARIANT
<222> LOCATION: 10
<223> OTHER INFORMATION: Xaa = Thr or Lys
<220> FEATURE:
<221> NAME/KEY: VARIANT
<222> LOCATION: 12
<223> OTHER INFORMATION: Xaa = Ala or Ser
<220> FEATURE:
<221> NAME/KEY: VARIANT
<222> LOCATION: 13
<223> OTHER INFORMATION: Xaa = Ser or Gly
<220> FEATURE:
<221> NAME/KEY: VARIANT
<222> LOCATION: 15
<223> OTHER INFORMATION: Xaa = Asp, Asn, Glu, or Ser
<220> FEATURE:
<221> NAME/KEY: VARIANT
<222> LOCATION: 22
<223> OTHER INFORMATION: Xaa = Lys or Gln
<220> FEATURE:
<221> NAME/KEY: VARIANT
<222> LOCATION: 24
<223> OTHER INFORMATION: Xaa = Thr or Ser
<220> FEATURE:
<221> NAME/KEY: VARIANT
<222> LOCATION: 25
<223> OTHER INFORMATION: Xaa = Asp or Asn
<220> FEATURE:
<221> NAME/KEY: VARIANT
<222> LOCATION: 27
<223> OTHER INFORMATION: Xaa = Val or Lys
<220> FEATURE:
<221> NAME/KEY: VARIANT
<222> LOCATION: 31
<223> OTHER INFORMATION: Xaa = Arg, Asn, or Gln
<220> FEATURE:
<221> NAME/KEY: VARIANT
<222> LOCATION: 34
<223> OTHER INFORMATION: Xaa = Asp or Asn

<400> SEQUENCE: 2

Xaa Leu Pro Ser Gly Trp Thr Xaa Leu Xaa Lys Xaa Xaa Asp Xaa Thr
 1               5                  10                  15

Thr Tyr Tyr Tyr Asn Xaa Thr Xaa Xaa Val Xaa Thr Asn Thr Xaa Pro
                20                  25                  30

Thr Xaa

<210> SEQ ID NO 3
<211> LENGTH: 34
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
```

```
<222> LOCATION: 1
<223> OTHER INFORMATION: Xaa = Ser, Asn, Asp, or Glu
<220> FEATURE:
<221> NAME/KEY: VARIANT
<222> LOCATION: 8
<223> OTHER INFORMATION: Xaa = Gln, Lys, Pro, Val, Glu, Arg, or Asn
<220> FEATURE:
<221> NAME/KEY: VARIANT
<222> LOCATION: 9
<223> OTHER INFORMATION: Xaa = Leu or Gln
<220> FEATURE:
<221> NAME/KEY: VARIANT
<222> LOCATION: 10
<223> OTHER INFORMATION: Xaa = Thr or Lys
<220> FEATURE:
<221> NAME/KEY: VARIANT
<222> LOCATION: 12
<223> OTHER INFORMATION: Xaa = Ala or Ser
<220> FEATURE:
<221> NAME/KEY: VARIANT
<222> LOCATION: 13
<223> OTHER INFORMATION: Xaa = Ser or Gly
<220> FEATURE:
<221> NAME/KEY: VARIANT
<222> LOCATION: 14, 25, 29, 34
<223> OTHER INFORMATION: Xaa = Asp or Asn
<220> FEATURE:
<221> NAME/KEY: VARIANT
<222> LOCATION: 15
<223> OTHER INFORMATION: Xaa = Asp, Asn, Glu, or Ser
<220> FEATURE:
<221> NAME/KEY: VARIANT
<222> LOCATION: 16
<223> OTHER INFORMATION: Xaa = Thr or Ser
<220> FEATURE:
<221> NAME/KEY: VARIANT
<222> LOCATION: 17
<223> OTHER INFORMATION: Xaa = Thr or Val
<220> FEATURE:
<221> NAME/KEY: VARIANT
<222> LOCATION: 19
<223> OTHER INFORMATION: Xaa = Tyr or Phe
<220> FEATURE:
<221> NAME/KEY: VARIANT
<222> LOCATION: 22
<223> OTHER INFORMATION: Xaa = Lys, Gln, or Glu
<220> FEATURE:
<221> NAME/KEY: VARIANT
<222> LOCATION: 24
<223> OTHER INFORMATION: Xaa = Thr or Ser
<220> FEATURE:
<221> NAME/KEY: VARIANT
<222> LOCATION: 26
<223> OTHER INFORMATION: Xaa = Val, Thr, or Gln
<220> FEATURE:
<221> NAME/KEY: VARIANT
<222> LOCATION: 27
<223> OTHER INFORMATION: Xaa = Val, Lys, or Thr
<220> FEATURE:
<221> NAME/KEY: VARIANT
<222> LOCATION: 28
<223> OTHER INFORMATION: Xaa = Thr or Gln
<220> FEATURE:
<221> NAME/KEY: VARIANT
<222> LOCATION: 31
<223> OTHER INFORMATION: Xaa = Arg, Asn, or Gln

<400> SEQUENCE: 3

Xaa Leu Pro Ser Gly Trp Thr Xaa Xaa Xaa Lys Xaa Xaa Xaa Xaa Xaa
 1               5                  10                  15

Xaa Tyr Xaa Tyr Asn Xaa Thr Xaa Xaa Xaa Xaa Xaa Xaa Thr Xaa Pro
            20                  25                  30

Thr Xaa

<210> SEQ ID NO 4
```

-continued

```
<211> LENGTH: 34
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 1
<223> OTHER INFORMATION: Xaa = Ser, Asn, or Asp
<220> FEATURE:
<221> NAME/KEY: VARIANT
<222> LOCATION: 8
<223> OTHER INFORMATION: Xaa = Gln or Lys
<220> FEATURE:
<221> NAME/KEY: VARIANT
<222> LOCATION: 10
<223> OTHER INFORMATION: Xaa = Thr or Lys
<220> FEATURE:
<221> NAME/KEY: VARIANT
<222> LOCATION: 12
<223> OTHER INFORMATION: Xaa = Ala or Ser
<220> FEATURE:
<221> NAME/KEY: VARIANT
<222> LOCATION: 13
<223> OTHER INFORMATION: Xaa = Ser or Gly
<220> FEATURE:
<221> NAME/KEY: VARIANT
<222> LOCATION: (14)...(15)
<223> OTHER INFORMATION: Xaa = Asp or Asn
<220> FEATURE:
<221> NAME/KEY: VARIANT
<222> LOCATION: 17
<223> OTHER INFORMATION: Xaa = Thr or Val
<220> FEATURE:
<221> NAME/KEY: VARIANT
<222> LOCATION: 19
<223> OTHER INFORMATION: Xaa = Tyr or Phe
<220> FEATURE:
<221> NAME/KEY: VARIANT
<222> LOCATION: 22
<223> OTHER INFORMATION: Xaa = Lys or Gln
<220> FEATURE:
<221> NAME/KEY: VARIANT
<222> LOCATION: 24
<223> OTHER INFORMATION: Xaa = Thr or Ser
<220> FEATURE:
<221> NAME/KEY: VARIANT
<222> LOCATION: 25
<223> OTHER INFORMATION: Xaa = Asp or Asn
<220> FEATURE:
<221> NAME/KEY: VARIANT
<222> LOCATION: 27
<223> OTHER INFORMATION: Xaa = Val or Lys
<220> FEATURE:
<221> NAME/KEY: VARIANT
<222> LOCATION: 28
<223> OTHER INFORMATION: Xaa = Thr or Gln
<220> FEATURE:
<221> NAME/KEY: VARIANT
<222> LOCATION: 31
<223> OTHER INFORMATION: Xaa = Arg or Asn
<220> FEATURE:
<221> NAME/KEY: VARIANT
<222> LOCATION: 34
<223> OTHER INFORMATION: Xaa = Asp or Asn

<400> SEQUENCE: 4

Xaa Leu Pro Ser Gly Trp Thr Xaa Leu Xaa Lys Xaa Xaa Xaa Xaa Thr
 1               5                  10                  15

Xaa Tyr Xaa Tyr Asn Xaa Thr Xaa Asp Val Xaa Xaa Asn Thr Xaa Pro
            20                  25                  30

Thr Xaa
```